(12) United States Patent
Chung et al.

(10) Patent No.: US 10,883,142 B2
(45) Date of Patent: Jan. 5, 2021

(54) RISK ASSESSMENT FOR PHENYTOIN-INDUCED ADVERSE DRUG REACTIONS

(71) Applicants: CHANG GUNG MEDICAL FOUNDATION CHANG GUNG MEMORIAL HOSPITAL AT KEELUNG, Keelung (TW); NATIONAL YANG-MING UNIVERSITY, Taipei (TW)

(72) Inventors: Wen-Hung Chung, Taoyuan County (TW); Shuen-Iu Hung, Taoyuan County (TW)

(73) Assignees: Chang Gung Medical Foundation Chang Gung Memorial Hospital at Keelung, Keelung (TW); National Yang-Ming University, Taipei (TW)

( * ) Notice: Subject to any disclaimer, the term of this patent is extended or adjusted under 35 U.S.C. 154(b) by 0 days.

(21) Appl. No.: 15/286,238

(22) Filed: Oct. 5, 2016

(65) Prior Publication Data
US 2017/0022561 A1    Jan. 26, 2017

Related U.S. Application Data

(60) Division of application No. 14/693,252, filed on Apr. 22, 2015, now abandoned, which is a continuation-in-part of application No. 13/323,515, filed on Dec. 12, 2011, now abandoned.

(51) Int. Cl.
*C12Q 1/6881* (2018.01)
*C12Q 1/6883* (2018.01)

(52) U.S. Cl.
CPC ......... *C12Q 1/6881* (2013.01); *C12Q 1/6883* (2013.01); *C12Q 2600/106* (2013.01); *C12Q 2600/118* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,582,908 B2 | 6/2003 | Fodor et al. | |
| 7,470,513 B2 | 12/2008 | Chen et al. | |
| 2006/0269935 A1 | 11/2006 | Tate et al. | |

FOREIGN PATENT DOCUMENTS

| | | | |
|---|---|---|---|
| CN | 1902328 A | 1/2007 | |
| WO | WO 2005/047544 A1 | 5/2005 | |
| WO | WO 2007/134235 A1 | 11/2007 | |
| WO | WO-2012174723 A1 * | 12/2012 | |

OTHER PUBLICATIONS

The Free Dictionary definition for "detectng", available via URL: <thefreedictionary.com/detecting>, printed on Nov. 14, 2017.*
Hirschhorn et al. Genetics in Medicine. vol. 4, No. 2, pp. 45-61, Mar. 2002.*
Lucentini et al The Scientist (2004) vol. 18, p. 20.*
Wall et al Nature Reviews Genetics (2003) 4:587-597.*
Zill et al. Molecular Psychiatry. 2004. 9: 1030-1036.*
Li et al BMC Genetics. 2010. 11:47.*
Gagneux et al Molecular Phylogenetics and Evolution. 2001. 18: 2-13.*
Takenaka et al PLOS One. Aug. 24, 2012. 7(8): e43461.*
Chung et al JAMA. Aug. 2014. 312(5): 525-534.*
Hung et al Pharmacogenetics and Genomics. Apr. 2006. 16(4): 297-306.*
Tanno et al Clin Transl Allergy. 2014 4(Suppl 3):p. 49.*
The Free Dictionary definition for "assaying", available via URL: <thefreedictionary.com/assaying>, printed on Jan. 30, 2018.*
Extended European Search Report in corresponding European Application No. EP11868033.9 dated Apr. 7, 2015, 20 pages.
William Kudzi et al., "Characterization of CYP2C9, CYP2C9 and CYP2C19 polymorphisms in a Ghanaian population", BMC Medical Genetics, Biomed Central, London, GB, vol. 10, No. 1, Dec. 2, 2009, 10:124; XP21066767; 6.
Robert T. Kinobe et al., "P450 2C18 Catalyzes the Metabolic Bioactivation of Phenytoin", Chemical Research in Toxicology, American Chemical Society, vol. 18, No. 12, Dec. 1, 2005; 1868-1875; XP 55145974; 8 pages.
Marisol Lopez et al., "Pharmacogenetics of the antiepileptic drugs phenytoin and lamotrigine", Drug Metabolism and Drug Interactions, vol. 26, No. 1, May 2011(May 2011)5-12; XP9180683; 8 pages.
Junji Saruwatari et al., "Update on the genetic polymorphisms of drug-metabolizing enzymes in antiepileptic drug therapy", Pharmaceuticals, M D P I AG, CH, vol. 3, No. 8, Aug. 20, 2010, 2709-2732; XP2702943, 24 pages.

(Continued)

*Primary Examiner* — Carla J Myers
(74) *Attorney, Agent, or Firm* — Pilloff Passino & Cosenza LLP; Sean A. Passino; Rachel K. Pilloff (57) ABSTRACT

A method of predicting the risk of a patient for developing phenytoin-induced adverse drug reactions (ADRs), including Stevens-Johnson syndrome (SJS), toxic epidermal necrolysis (TEN), or drug reactions with eosinophilia and systemic symptoms (DRESS) is disclosed. Genetic polymorphisms of CYP2C genes (including rs1057910 (CYP2C9*3) and rs3758581 on CYP2C19), and HLA alleles (including HLA-B*1502, HLA-B*1301, and HLA-B*5101) can predict adverse reactions caused by phenytoin or fosphenytoin. Accordingly, the present invention provides a kit to assess the risk of a patient for developing adverse reactions in response to phenytoin-related drugs, which comprises the determination of the presence of a specific allele selected from the group consisting of rs1057910 (CYP2C9*3), rs3758581 on CYP2C19, HLA-B*1502, HLA-B*1301, and HLA-B*5101, wherein the presence of at least one allele is indicative of a risk for the adverse drug reactions.

2 Claims, 2 Drawing Sheets

(56) References Cited

OTHER PUBLICATIONS

Joyce A. Goldstein, "Clinical relevance of genetic polymorphisms in the human CYP2C subfamily", British Journal of Clinical Pharmacology, Blackwell Scientific Publ., GB, vol. 52, No. 4, Oct. 1, 2001, 349-355; XP1121634, 7 pages.
Wolfgang Loscher et al., "The clinical impact of pharmacogenetics on the treatment of epilepsy", Pharmacogenetics in Epilepsy, Epilepsia, vol. 50, No. 1, Jan. 1, 2009; 1-23, XP55145800; 23 pages.
Ulrich Klotz, "The Role of Pharmacogenetics in the Metabolism of Antiepileptic Drugs, Pharmacokinetic and therapeutic Implications", Pharmacogenetics in the Metabolism of Antiepileptics, Clinical Pharmacokinetics, vol. 46, No. 4, 2007; 271-279; XP9180697, 9 pages.
Renato Brandolese, M.D. et al., "Severe phenytoin intoxication in a subject homozygous for CYP2C9*3", Clinical Pharmacology and Therapeutics, Nature Publishing Group, U.S. Grand Rounds, Oct. 1, 2001, p. 391-394, KP57 43723, 4 pages.
Ai-Young Lee et al., "Genetic Polymorphism of cytochrome P450 2C9 in diphenylhydantoin-induced cutaneous adverse drug reactions", European Journal of Clinical Pharmacology, vol. 60, No. 3, May 1, 2004, 155-159; XP 55146123, 5 pages.
Shuen-lu Hung et al., "Common risk allele in aromatic antiepileptic-drug induced Stevens-Johnson syndrome and toxic epidermal necrolysis in Han Chinese", Pharmacogenomics, vol. 11, No. 3, Mar. 2010, 349-356; XP008173148; 8 pages.
Celeste B. L. Man, et al., "Association between HLA-B*1502 Allele and Antiepileptic Drug-Induced Cutaneous Reactions in Han Chinese", Epilepsia, vol. 48, No. 5, May 14, 2007, 1015-1018; XP55176743 (4 pages).
Mark McCormack et al., "Genome-wide mapping for clinically relevant predictors of lamotrigine- and phenytoin-induced hypersensitivity reactions", Pharmacogenomics, vol. 13, No. 4, Mar. 1, 2012, 399-405, XP55176757; 7 pages.
Office Action in corresponding Japanese Application No. 2014-516152 dated Mar. 10, 2015, 6 pages.
Kan Chiba, "Genetic polymorphisms of the human CYP2C subfamily", Folia Pharmacol. Jpn. (Nippon Yakurigaku Zasshi); vol. 112, p. 15-21, 1998, 7 pages.
Masato Taguchi et al., "Evaluation of Phenytoin Dosage Regimens Based on Genotyping of CYP2C Subfamily in Routinely Treated Japanese Patients", Drug Metab. Pharmacokinet, vol. 20, No. 2, 2005, 107-112, 6 pages.
C. Depondt et al., "A candidate gene study of antiepileptic drug tolerability and efficacy identifies an association of CYP2C9 variants with phenytoin toxicity", European Journal of Neurology, Pharmacogenomics, vol. 18, 2011, 1159-1164, 7 pages.
International Search Report for PCT application No. PCT/CN2011/076187 dated Apr. 5, 2012, 4 pages.
Written Opinion of Intellectual Property Office of Singapore (IPOS) for Application No. 10201502502Y dated Jan. 7, 2016, 5 pages.
Search Report of Intellectual Property Office of Singapore (IPOS) for Application No. 10201502502Y dated Nov. 23, 2015, 3 pages.
Written Opinion of Intellectual Property Office of Singapore (IPOS) for Application No. 201309216-8 dated Oct. 8, 2014, 7 pages.
J. T. Wilson et al., "High incidence of a concentration-dependent skin reaction in children treated with phenytoin", British Medical Journal, Jun. 17, 1978, 1583-1586 (4 pages).
Michiko Aihara, "Pharmacogenetics of cutaneous adverse drug reactions", Journal of Dermatology, 2011; 38: 246-254, 9 pages.
Nada Bozina et al., "Genetic polymorphism of metabolic enzymes P450 (CYP) as a susceptibility factor for drug response, toxicity, and cancer risk", Arh Hig Rada Toksiko, 2009; 60: 217-242, 26 pages.
Yoshiki Ito et al., "High-throughput DNA typing of HLA-A, -B, -C, and -DRB1 Loci by a PCR-SSOP-Luminex method in the Japanese population", Immunogenetics, 2005, 57: 717-729, 13 pages.
Eric Mick et al., "Genome-Wide Association Study of Response to Methylphenidate in 187 Children With Attention-Deficit/Hyperactivity Disorder", American Journal of Medical Genetics Part B (Neuropsychiatric Genetics), 2008, 1478: 1412-1428, 7 pages.
TSGH Pharmacy Newsletter Apr. 2003, 6 pages.
Cheng et al., "Recent Advance on the Association Between HLA-B*1502 Allele and Severe Cutaneous Adverse Reactions in Different Race Induced by Anti-epileptic Drugs," Chinese Journal of Pharmacovigilance, vol. 8, No. 4, Apr. 2011, w/English Translation (9 pages).

* cited by examiner

RISK ASSESSMENT FOR PHENYTOIN-INDUCED ADVERSE DRUG REACTIONS

CROSS-REFERENCE TO RELATED APPLICATIONS

This application is divisional application of U.S. application Ser. No. 14/693,252, filed Apr. 22, 1015, which is a continuation-in-part of U.S. application Ser. No. 13/323,515, filed Dec. 12, 2011. The disclosures of all of which are incorporated by reference herein in their entirety.

FIELD OF THE INVENTION

The present invention is related to a method for predicting the risk of a patient for adverse drug reactions, and more particularly to a risk assessment for developing adverse drug reactions in response to phenytoin.

BACKGROUND OF THE INVENTION

Adverse drug reactions (abbreviated ADRs) are expressions that describe harm associated with the use of given medication at a normal dosage. Drug hypersensitivity is a common adverse event during medical treatments and contributes to about 20% of reported ADRs. These hypersensitivity reactions may present from mild skin rash (MPE) to life-threatening drug reaction with eosinophilia and systemic symptoms (DRESS), Stevens-Johnson syndrome (SJS), or toxic epidermal necrolysis (TEN).

Many aromatic antiepileptic drugs (AEDs), such as phenytoin, carbamazepine or lamotrigine, are frequently associated with hypersensitive reactions. In particular, phenytoin is a first-line AED, however, more than 19% of patients received phenytoin developed hypersensitivity reactions. Previous studies showed that the deficiency of microsomal epoxide hydroxylase and human leukocyte antigen (HLA) subtypes may associate with AED hypersensitivity. However, the relationship between drug metabolism/genetic susceptibility and phenytoin-induced hypersensitivity reactions is still unclear.

Therefore, there remains a need for a new and improved method for predicting the risk of phenytoin-induced hypersensitivity, wherein the risk can be assessed by evaluating the factors including genetic polymorphisms of CYP2C9, phenytoin plasma concentration and HLA genotypes.

SUMMARY OF THE INVENTION

The present invention provides a method of predicting the risk of a patient for developing phenytoin-related adverse drug reactions, particularly the severe cutaneous adverse reactions (SCAR), including SJS, TEN and DRESS. This invention provides kits which test the presence of specific alleles of CYP2C and HLA genes, can be used to avoid the occurrence of phenytoin-induced SJS/TEN/DRESS.

This invention identified that variants of rs1057910 (CYP2C9*3) and rs3758581 on CYP2C genes in a patient increased the risk of phenytoin-induced severe cutaneous adverse reactions. Patients with these variants showed delayed clearance of the drugs, and developed phenytoin-related severe cutaneous adverse reactions. In addition to rs1057910 (CYP2C9*3) and rs3758581, other variants affecting CYP2C enzyme activity or forming haplotypes are also the predictors of phenytoin-induced SCAR. These variants included rs17110192, rs7896133 on CYP2C18; rs17110321, rs9332093, rs9332245 on CYP2C9; rs3758581, rs2860905, rs4086116 on CYP2C19 and rs7899038, rs1592037, rs1934952, rs11572139, rs6583967 on CYP2C8, and rs2274222, rs11188183, rs7921561, rs10882544, rs7084271, rs644437, rs12769577, rs617848, rs10882551, rs585381, rs648638, rs664093, rs12262878, rs17524438, rs12413028, rs11188246, rs12415795, rs11596107, rs11596737, rs10509685, rs7912686, rs17453729, rs17453764, rs17526000 and rs12769370 on the nearby regions.

In addition to rs1057910 (CYP2C9*3) and rs3758581, this invention identified specific HLA alleles, including HLA-A*0207, HLA-A*2402, HLA-B*1301, HLA-B*1502, HLA-B*4001, HLA-B*4609, HLA-B*5101, HLA-DRB1*1001 and HLA-DRB1*1502 were significantly associated with phenytoin-induced ADRs (SJS/TEN, DRESS, or MPE). In particular, three HLA alleles: HLA-B*1502, HLA-B*1301, and HLA-B*5101, could be used as the predictors of phenytoin-induced SCAR.

Accordingly, the present application provides a method of assessing the risk of a patient for developing cutaneous adverse reactions in response to drugs, in which the method detects the presence of a specific allele using a biological sample from the patient. The method detects the presence of a specific allele in a panel of variants comprising rs1057910 (CYP2C9*3), rs3758581 on CYP2C19, HLA-B*1502, HLA-B*1301, and HLA-B*5101. The drug is preferably selected from the group of aromatic anticonvulsants. Most preferably, the drug is phenytoin or fosphenytoin.

Specifically, one aspect of the present invention provides a kit to assess the risk of a patient for developing adverse reactions in response to phenytoin-related drugs, which comprises the determination of the presence of a specific allele selected from the group consisting of rs1057910 (CYP2C9*3), rs3758581 on CYP2C19, HLA-B*1502, HLA-B*1301, and HLA-B*5101, wherein the presence of at least one allele is indicative of a risk for the adverse drug reactions. The drug is preferably selected from the group consisting of aromatic anticonvulsants. Most preferably, the drug is phenytoin or fosphenytoin.

The adverse drug reaction is preferably a cutaneous adverse reaction, such as Stevens-Johnson syndrome, toxic epidermal necrolysis, drug reaction with eosinophilia and systemic symptoms, or maculapapular eruption. In a preferred embodiment, the drug is phenytoin or fosphenytoin, and the panel of kit detecting rs1057910 (CYP2C9*3), rs3758581 on CYP2C19, HLA-B*1502, HLA-B*1301, and HLA-B*5101.

The specific allele can be detected by using any method known in the art. For example, the presence of the allele can be determined by using oligonucleotide primers and probes that specifically hybridize with the nucleic acid and amplify the fragment for the allele. Preferably, the DNA prepared from the peripheral blood of the patient is employed in the method of detection. In addition, the allele can also be detected by, for example, serological, microcytotoxicity, or antibodies methods.

The presence of the allele can also be determined by detecting an equivalent genetic marker of the allele, which is a genetic marker that is linked to the allele. For example, the CYP2C-markers of rs1057910 (CYP2C9*3) haplotype include, without being limited to, rs17110192, rs3758581, rs17110321, rs9332093, rs9332245, rs1592037, rs6583967, rs10882551, and rs12262878. The markers of HLA-B B*1502 haplotype comprise, without being limited to, DRB1*1202, CW*0801, CW*0806, A*1101, and MICA*019. In other words, the presence of the alleles on the haplotypes of rs1057910 (CYP2C9*3), rs3758581, HLA-B*1502, HLA-B*1301, or HLA-B*5101, rather than the alleles per se, is indicative of a risk for adverse drug reactions.

Another aspect of the present invention provides a method of pharmacogenomics profiling comprising determining the presence of at least one allele selected from the group consisting of rs1057910 (CYP2C9*3), rs3758581 on CYP2C19, HLA-B*1502, HLA-B*1301, and HLA-B*5101. Preferably, the presence of at least one allele selected from the group is determined, such as rs1057910 (CYP2C9*3). More preferably, the presence of all five alleles is determined. The method can optionally comprise the determination of other risk factors. Those other risk factors may be associated with the predisposition for any disease or medical condition, including adverse drug reactions. Further provided is a method of screening and/or identifying medicines that can be used to treat drug-induced severe cutaneous adverse reactions by using CYP2C9 and HLA-B alleles as a target in drug development.

A method of assessing a risk of a human patient for developing an adverse reaction in response to a drug, comprising detecting the presence of a specific allele selected from a panel of CYP2C and HLA-B variants in a sample obtained from the patient, and correlating the presence of the specific allele in the sample with an increased risk for an adverse reaction in the patient in response to the drugs, wherein the adverse reaction is Stevens-Johnson syndrome, toxic epidermal necrolysis or drug reactions with eosinophilia and systemic symptoms, and wherein the drug is selected from a group consisting of phenytoin or fosphenytoin.

Wherein detecting the presence of the specific allele is selected from a panel of variants comprising rs1057910 (CYP2C9*3), rs3758581, HLA-B*1301, and HLA-B*5101.

Wherein the specific allele is the equal variant of haplotypes or biological function of the rs1057910 (CYP2C9*3) or rs3758581 or HLA-B*1301 or HLA-B*5101.

Wherein either one, two, three, four variants or the combination proves the presence of a specific allele.

Wherein the presence of the allele is determined by using oligonucleotides that specifically hybridizes to the allele.

Wherein the sample obtained from the patient is a DNA sample or RNA or protein or cells or sera from peripheral blood or saliva or urine or hair of the patient.

Wherein the adverse drug reaction is Stevens-Johnson syndrome or toxic epidermal necrolysis or drug reactions with eosinophilia and systemic symptoms.

A kit of detecting a risk of a human patient for developing an adverse reaction in response to phenytoin or fosphenytoin, comprising at least one oligonucleotide primer that hybridize to the risk genes and relevant regions and use of polymerase chain reaction (PCR) to amplify the specific fragment, an oligonucleotide probe that binds specifically to the allele.

Wherein the kit preferably contains reagents for detecting the probe.

Wherein there are two to eight oligonucleotide primers.

Wherein the kits further comprise the PCR primers suitable for each and every allele.

Wherein the kits further comprise tools and reagents for collecting biological samples from patients, as well as those for preparing genomic DNA, cDNA, RNA or the allele protein from the samples.

Wherein the kits include PCR primers for amplifying the relevant regions and risk genes of the genomic DNA.

Wherein detecting the presence of the specific allele selected from a panel of variants comprising CYP2C and HLA-B variants in a sample obtained from the patient, and correlating the presence of the specific allele in the sample with an increased risk for an adverse reaction in the patient in response to the drugs, wherein the adverse reaction is Stevens-Johnson syndrome, toxic epidermal necrolysis or drug reactions with eosinophilia and systemic symptoms.

Wherein detecting the presence of the specific allele selected from a panel of variants comprising rs1057910 (CYP2C9*3), rs3758581, HLA-B*1301, and HLA-B*5101.

Wherein the specific allele is the equal variant of haplotypes or biological function of the rs1057910 (CYP2C9*3) or rs3758581 or HLA-B*1301 or HLA-B*5101.

Wherein either one, two, three, four variants or the combination proves the presence of a specific allele.

Wherein the presence of the allele is determined by using oligonucleotides that specifically hybridizes to the allele.

Wherein the sample obtained from the patient is a DNA sample or RNA or protein or cells or sera from peripheral blood or saliva or urine or hair of the patient.

Wherein the adverse drug reaction is Stevens-Johnson syndrome or toxic epidermal necrolysis or drug reactions with eosinophilia and systemic symptoms.

DETAILED DESCRIPTION OF THE INVENTION

The present invention provides a method for accessing the risk of a patient for developing phenytoin-induced adverse drug reactions, particularly for SJS, TEN, and DRESS that are severe cutaneous adverse reactions. It was discovered that phenytoin-related severe cutaneous adverse reactions is associated with specific alleles (rs1057910 (CYP2C9*3), rs3758581) on CYP2C genes and HLA-B*1502, HLA-B*1301, and HLA-B*5101. The correlation with rs1057910 (CYP2C9*3) is most significant with phenytoin-related SCAR. Preferably, the presence of at least one allele selected from the group is determined, such as rs1057910 (CYP2C9*3). More preferably, the presence of all five alleles is determined.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The diagnosis of Stevens-Johnson syndrome (SJS) and toxic epidermal necrolysis (TEN) were based on the clinical morphology defined by consensus criteria (Bastuji-Garin S, Rzany B et al, 1993). SJS is defined as skin detachment of <10% of body-surface area, overlap SJS_TEN as skin detachment of 10-29% and TEN as >/=30%. The criteria for DRESS were cutaneous rash (e.g. diffuse macuopapular, exfoliative dermatitis) with symptoms of eosinophilia, atypical circulating lymphocytes, acute hepatocellular injury, or worsening renal function (Kardaun S H, Sidoroff A et al, 2007). Patients who fulfilled the diagnostic criteria of SJS, TEN, or DRESS induced by phenytoin were identified in Chang Gung Memorial Hospital Health System and were enrolled for this study.

Figure 1:
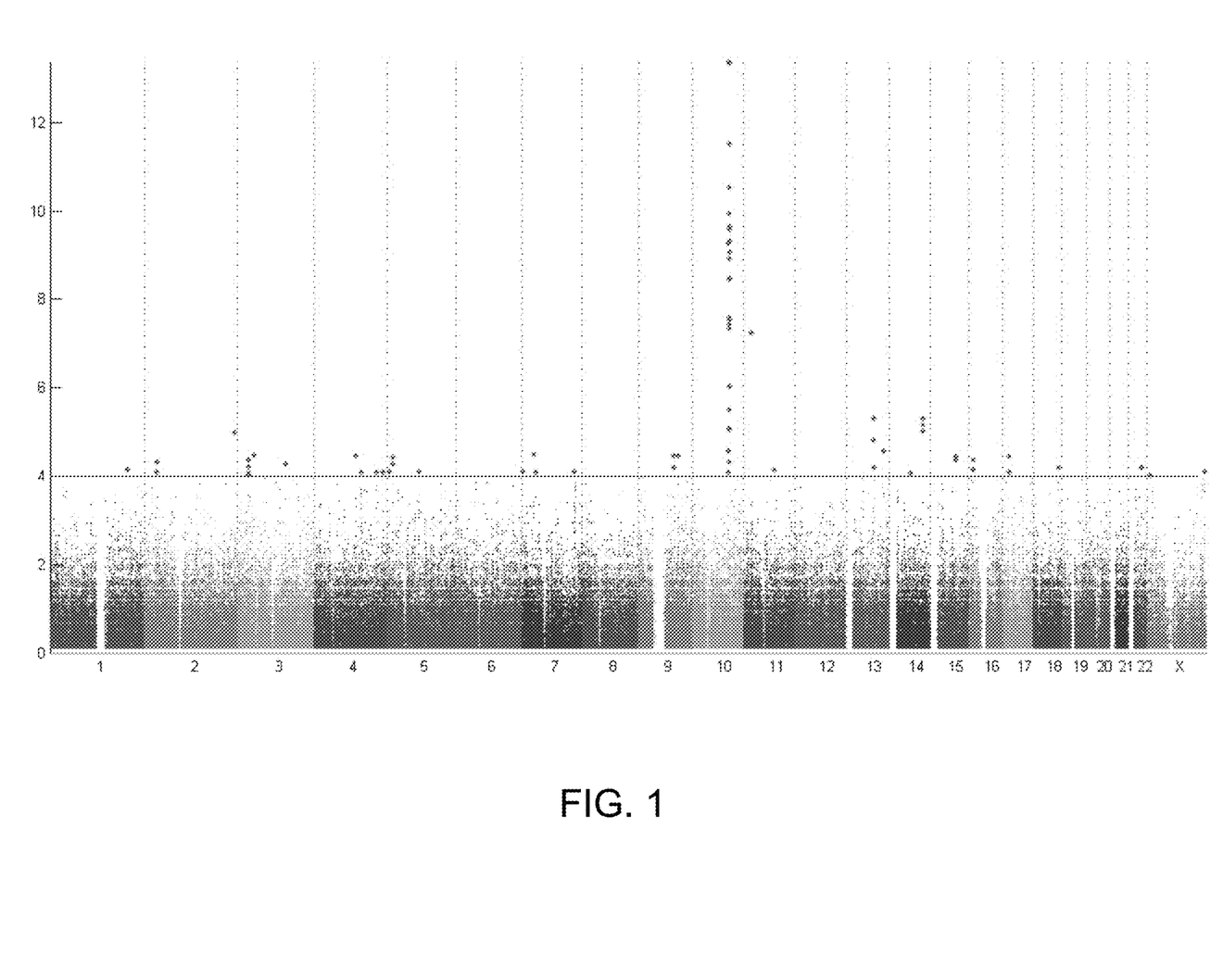
FIG. 1 illustrates the genome-wide association study of phenytoin-induced SCARs, where each dot represents a SNP. The x-axis represents the position of the SNP on chromosomes, while the y-axis represents the $-\log_{10}$ P value of the SNP in the case-control association study. 58 phenytoin-induced SJS/TEN/DRESS and 198 population controls are included in the study. SNPs with P values $<10^{-6}$ is highlighted in red. The strong signal in chromosome 10 lies in the CYP2C region.

We first performed genome-wide association study on 58 patients with phenytoin-induced adverse drug reactions and 198 controls. The results indicate that many variants (including rs17110192, rs17110321, rs9332093, rs9332245, rs1592037, rs6583967, rs10882551, and rs12262878.) on CYP2C genes are strongly associated with phenytoin-induced SCAR (FIG. 1).

To discover exonic SNPs, we designed PCR primers and directly sequenced the CYP2C genes of 90 SCAR cases. Furthermore, we designed the oligonucleotide primers and probes as kits to validate the association between 90 cases and 130 tolerant controls. We identified two nonsynonymous variants, rs1057910 (CYP2C9*3, p.I359L) and rs3758581 (p.V331I), which showed the significant association with phenytoin SCAR (rs1057910 (P=5.70×10$^{-12}$, OR (95% CI)=24.51 (7.22 to 83.23); rs3758581 (P=5.20×10$^{-11}$, OR (95% CI)=13.78 (5.48 to 34.62)). We also identified additional 11 nonsynonymous SNPs, including 2 nonsense SNPs (rs4986893 and rs41291550) and 9 missense SNPs, and one synonymous SNP (rs4244285) which causes a splicing defect on CYP2C19. Seven haplotypes were inferred from these SNPs. These variants on CYP2C genes can be considered as equal alleles on the haplotypes of rs1057910 (CYP2C9*3, p.I359L) and rs3758581 as they showed a strong linkage disequilibrium (LD) block.

Accordingly, in one embodiment, this invention provide a method and kits for accessing the risk of a patient for developing phenytoin-induced adverse drug reactions comprises the step of detecting the presence of SNPs (Single Nucleotide Polymorphism) on chromosome 10 in the CYP2Cs region, which included rs17110192, rs7896133 on CYP2C18; rs17110321, rs9332093, rs9332245 on CYP2C9; rs3758581, rs2860905, rs4086116 on CYP2C19 and rs7899038, rs1592037, rs1934952, rs11572139, rs6583967 on CYP2C8 (see Table 1). The other SNPs which located nearby CYP2C loci, such as rs2274222, rs11188183, rs7921561, rs10882544, rs7084271, rs644437, rs12769577, rs617848, rs10882551, rs585381, rs648638, rs664093, rs12262878, rs17524438, rs12413028, rs11188246, rs12415795, rs11596107, rs11596737, rs10509685, rs7912686, rs17453729, rs17453764, rs17526000 and rs12769370.

In another embodiment, the method for accessing the risk of a patient for developing phenytoin-induced adverse drug reactions comprises the step of combining rs1057910 (CYP2C9*3), rs3758581, rs17110192, rs9332245 or rs1592037 (especially for rs17110192, rs1057910 and rs3758581) belonging to a haplotype that can increase the statistical significance of association with phenytoin-induced SJS/TEN/DRESS comparing to phenytoin tolerant controls. There was no phenytoin tolerant individuals carried the combination of rs1057910, rs3758581, rs17110192, rs9332245 or rs1592037 (especially for rs1057910 and rs3758581, 0/95), however, near one third of phenytoin hypersensitivity patients carried this combination (30/96). Some of these SNPs cause a change in the amino acid sequence. For example, rs3758581, a missense change in CYP2C19 exon7 was significantly associated with phenytoin-SJS/TEN/DRESS. It is further discovered that CYP2C9*3 has a strong association with phenytoin-induced SJS/TEN/DRESS.

In another embodiment, the present invention provides a method and kits for accessing the risk of a patient for developing phenytoin-induced adverse drug reactions comprising utilizing a candidate genes (CYP2Cs and HLA) approach of 152 patients with phenytoin-induced hypersensitivity reactions, including 53 cases of phenytoin-SJS/TEN, 24 cases of phenytoin-DRESS and 75 cases of phenytoin-MPE as well as 118 tolerant controls that received phenytoin more than 3 months without any adverse reaction. The result showed there are up to 30.2% of phenytoin-SJS/TEN and 37.5% of phenytoin-DRESS carried CYP2C9*3 genotype. In comparison, 14.7% of phenytoin-MPE and only 2.5% of tolerant controls carried CYP2C9*3. The present invention also indicates that genetic variants in CYP2C9 as well as in CYP2C19, CYP2C8 and CYP2C18 are related to poor metabolic activity for phenytoin and increase drug accumulation in plasma that leads to hypersensitivity reactions. In addition to the genetic link in CYP2Cs, HLA-A*0207, HLA-A*2402, HLA-B*1301, HLA-B*1502, HLA-B*4001, HLA-B*4609, HLA-B*5101, HLA-DRB1*1001 or HLA-DRB1*1502 also showed significant association with phenytoin-induced hypersensitivity. Thus, these data revealed that the genetic polymorphisms of CYP2C9/2C19/2C8/2C18 or its defective alleles, the phenytoin plasma levels and specific HLA genotypes all contribute to phenytoin induced severe cutaneous adverse drug reactions.

It was discovered that specific CYP2C genetic variants, including CYP2C9, CYP2C19, CYP2C8 and CYP2C18 were related to low metabolic activity of phenytoin and was associated with phenytoin-induced hypersensitivity reactions. In addition to CYP2C variants, HLA-A*0207, HLA-A*2402, HLA-B*1301, HLA-B*1502, HLA-B*4001, HLA-B*4609, HLA-B*5101, HLA-DRB1*1001 or HLA-DRB1*1502 were also discovered to show significant association with phenytoin-induced hypersensitivity or cutaneous adverse drug reactions. It is noted that "phenytoin" in the present invention may also include pheytoin-related anticovulsant drugs including fosphenytoin.

Kits

The present invention provides kits comprising the means for detecting at least one allele selected from the group consisting of rs1057910 (CYP2C9*3), rs3758581 on CYP2C19, HLA-B*1502, HLA-B*1301, and HLA-B*5101. The means of a kit is preferably two to eight oligonucleotide primers that hybridize to the risk genes and relevant regions and use of polymerase chain reaction to amplify the specific fragment. A kit further comprises an oligonucleotide probe that binds specifically to the allele, and the kit preferably contains reagents for detecting the probe. The probes are preferably oligonucleotides. The kits further comprise tools and/or reagents for collecting biological samples from patients, as well as those for preparing genomic DNA, cDNA, RNA or the allele protein from the samples. For example, the kits include PCR primers for amplifying the relevant regions and risk genes of the genomic DNA. The kits preferably comprise means for detecting at least one allele selected from the group consisting of rs1057910 (CYP2C9*3), rs3758581 on CYP2C19, HLA-B*1502, HLA-B*1301, or HLA-B*5101. Optionally, the kits comprise means for detecting other genetic factors those useful in pharmacogenomic profiling. Thus, in a preferred embodiment, the kits comprise oligonucleotide primers and probes for detecting all five risk alleles, rs1057910 (CYP2C9*3), rs3758581 on CYP2C19, HLA-B*1502, HLA-B*1301, and HLA-B*5101. More preferably, the kits further comprise the PCR primers suitable for each and every allele. The following examples are offered to illustrate this invention and are not to be construed in any way as limiting the scope of the present invention. While this invention is particularly shown and described with references to preferred embodiments thereof, it will be understood by those skilled in the art that various changes in form and details may be made therein without departing from the spirit and scope of the invention as defined by the appended claims.

EXAMPLES

Example 1

Variants on CYP2C Genes and Phenytoin-Related SCAR

In the cohort of 168 individuals with phenytoin-related ADRs, 90 cases were diagnosed to have S] S/TEN/DRESS and 78 individuals had milder cutaneous adverse drug reactions (erythema multiform, maculopapular rash or fixed drug eruption). The control group consisted of 198 subjects. By using genome wide association study (Affymetrix 6.0) of 58 phenytoin-induced SCARs (including SJS, TEN, and DRESS) and 198 population controls, it is found that the most significant SNPs were in chromosome 10 (see FIG. 1) of the CYP2C region, such as rs17110192, rs7896133 on CYP2C18; rs17110321, rs9332093, rs9332245 on CYP2C9; rs3758581, rs2860905, rs4086116 on CYP2C19 and rs7899038, rs1592037, rs1934952, rs11572139, rs6583967 on CYP2C8 (see Table 1). The other SNPs which located nearby CYP2C loci, such as rs2274222, rs11188183, rs7921561, rs10882544, rs7084271, rs644437, rs12769577, rs617848, rs10882551, rs585381, rs648638, rs664093, rs12262878, rs17524438, rs12413028, rs11188246, rs12415795, rs11596107, rs11596737, rs10509685, rs7912686, rs17453729, rs17453764, rs17526000 and rs12769370 were also significantly associated with phenytoin-induced hypersensitivity reactions (see Table 1). To discover exonic SNPs, we designed PCR primers and directly sequenced the CYP2C genes of 90 SCAR cases. Furthermore, we designed the oligonucleotide primers and probes as kits to validate the association between 90 cases and 130 tolerant controls. We identified two nonsynonymous variants, rs1057910 (CYP2C9*3, p.I359L) and rs3758581 (p. V331I), which showed the significant association with phenytoin SCAR (rs1057910 (P=5.70×10$^{-12}$, OR (95% CI)=24.51 (7.22 to 83.23); rs3758581 (P=5.20×10$^{-11}$, OR (95% CI)=13.78 (5.48 to 34.62)) (Reference 9: Chung W H, JAMA 2014). Seven haplotypes were inferred from these SNPs. These variants on CYP2C genes can be considered as equal alleles on the haplotypes of rs1057910 (CYP2C9*3, p.I359L) and rs3758581 as they showed a strong linkage disequilibrium (LD) block. Accordingly, the present invention provides a method of assessing the risk of phenytoin-induced adverse drug reactions comprising the step of determining the presence of variants in chromosome 10 of the CYP2C region, including CYP2C9, CYP2C19, CYP2C8 and CYP2C18.

By this genotyping test, we can directly detect the specific SNPs which are associated with PHT-induced ADR on a chip. It will lower the cost and save time in comparison with Affymetrix 6.0 assay.

Preferably, the presence of the allele is determined by using oligonucleotides that specifically hybridizes to the allele.

Previous study indicated that CYP2C9*3 increased the risk of phenytoin-induced maculopapular exanthem (MPE) (Lee A Y. et al. 2004). However, maculopapular exanthema is different from SCAR. In one embodiment, CYP2C9*3 is used to predict the risk of phenytoin-induced adverse drug reactions. To examine the role of CYP2C9*3 on other types of phenytoin-induced adverse drug reactions (ADRs), especially for the unique mucocutaneous blistering phenotypes of SJS or TEN, a single nucleotide polymorphism (SNP) genotyping has been conducted on patients with adverse drug reactions induced by phenytoin. 152 patients were enrolled for the study of phenytoin-induced hypersensitivity reactions, including 53 cases of phenytoin-SJS/TEN, 24 cases of phenytoin-DRESS and 75 cases of phenytoin-MPE, as well as 118 tolerant controls that received phenytoin more than 3 months without any adverse reaction. The results showed that CYP2C9*3 variant was present in 16 of 53 (30.2%) phenytoin-induced SJS/TEN patients, 9 of 24 (37.5%) phenytoin-induced DRESS patients and 11 of 75 (14.7%) phenytoin-induced MPE. In comparison, the variant was only found in 2.5% (3/118) of the phenytoin-tolerant group (see Table 2). Statistical analysis of phenytoin hypersensitivity cases and tolerant controls showed that CYP2C9*3 was most significantly associated with phenytoin induced SJS/TEN (SJS/TEN vs. tolerant controls: P=3.3×10$^{-7}$, OR=17.5 (4.8-63.7) or DRESS (DRESS vs. tolerant controls: P=6.1×10$^{-5}$, OR=19.2 (4.4-82.7)), but only weakly associated with phenytoin-MPE (MPE vs. tolerant control: P=0.004, OR=6.2 (1.6-23.3)), suggesting that the presence of this CYP2C9*3 variant can be used in the identification of high-risk patients for phenytoin-induced ADRs, particularly phenytoin-induced SJS/TEN or DRESS.

In another embodiment, the SNPs on CYP2C causing the amino acid to change can also be used for assessing the risk of phenytoin-induced adverse drug reactions. A further study has been conducted for some SNPs on CYP2C genes which can make amino acid changed, such as 371G>A (rs12414460, Arg124Gln), 895A>G, (rs72558192, Thr299Ala, known as CYP2C9*16), 1362G>C (Gln454His, known as CYP2C9*19) on CYP2C9; 991A>G (rs3758581, Ile331Val), 395G>A (rs72558184, Arg132Gln, known as CYP2C19*6), 636G>A (rs4986893, Trp212end, known as CYP2C19*3), 681G>A, (rs4244285, causing splicing site mutation, known as CYP2C19*2), 781C>T (Arg261Trp) on CYP2C19 and 204T>A (rs41291550, Tyr68end), 370C>T (Arg124Trp), 576G>C (Gln192His), 1154C>T (rs2281891, Thr385Met) on CYP2C18. These changes of CYP2C enzyme can affect both its activity and its substrate specificity. For example, rs3758581, a missense change in CYP2C19 exon7 was significantly associated with phenytoin-SJS/TEN/DRESS (SJS/TEN/DRESS vs. Tolerant: P=0.0003, OR=7.28 (2.3564-22.4912)) (see Table 1).

TABLE 1

List of SNPs of CYP2C loci in chromosome 10 significantly associated with phenytoin-SJS/TEN/DRESS

| RS# | Annotation | Chr | % A, B Fisher_P | OR |
|---|---|---|---|---|
| rs17110192 | CYP2C18 | 10 | 4.03E-14 | 13.33333 |
| rs7896133 | CYP2C18 | 10 | 1.14E-06 | 0.115132 |
| rs17110321 | CYP2C9 | 10 | 4.03E-14 | 0.075 |
| rs9332093 | CYP2C9 | 10 | 1.19E-13 | 13.00438 |
| rs9332245 | CYP2C9 | 10 | 4.37E-13 | 12.5 |
| rs2860905 | CYP2C19 | 10 | 1.14E-06 | 0.115132 |
| rs4086116 | CYP2C19 | 10 | 3.49E-05 | 7.6 |
| rs3758581 | CYP2C19 | 10 | 3.00E-04 | 7.28 |
| rs7899038 | CYP2C8 | 10 | 1.87E-07 | 0.078083 |
| rs1592037 | CYP2C8 | 10 | 4.92E-13 | 11.67059 |
| rs1934952 | CYP2C8 | 10 | 7.39E-10 | 6.441558 |
| rs11572139 | CYP2C8 | 10 | 6.38E-06 | 15.32967 |
| rs6583967 | CYP2C8 | 10 | 4.92E-13 | 11.67059 |
| rs11188183 | chromosome 10 open reading frame 129 | 10 | 3.06E-12 | 0.083365 |
| rs7921561 | chromosome 10 open reading frame 129 | 10 | 5.52E-13 | 11.6098 |
| rs644437 | chromosome 10 open reading frame 129 | 10 | 4.92E-13 | 11.67059 |
| rs12769577 | chromosome 10 open reading frame 129 | 10 | 4.92E-13 | 11.67059 |
| rs10882551 | chromosome 10 open reading frame 129 | 10 | 4.96E-14 | 14.61539 |
| rs585381 | chromosome 10 open reading frame 129 | 10 | 4.31E-12 | 0.096042 |
| rs648638 | chromosome 10 open reading frame 129 | 10 | 4.92E-13 | 11.67059 |
| rs664093 | chromosome 10 open reading frame 129 | 10 | 4.92E-13 | 0.085685 |
| rs12262878 | chromosome 10 open reading frame 129 | 10 | 1.67E-13 | 12.76471 |
| rs17524438 | chromosome 10 open reading frame 129 | 10 | 1.26E-12 | 0.0875 |

TABLE 2

CYP2C9*3 frequency in 152 patients with phenytoin-induced cutaneous ADRs and 118 tolerant controls.

| CYP2C9 Genotypes | CYP2C9*1 | CYP2C9*3 § | Total |
|---|---|---|---|
| SJS/TEN | 37 (69.8%) | 16 (30.2%) | 53 |
| DRESS | 15 (62.5%) | 9 (37.5%) | 24 |
| MPE | 64 (85.3%) | 11 (14.7%) | 75 |
| Tolerance | 115 (97.5%) | 3 (2.5%) | 118 |

§ SJS/TEN vs. Tolerant: P = $3.3 \times 10^{-7}$, OR = 17.5 (4.8-63.7); DRESS vs. Tolerant: P = $6.1 \times 10^{-5}$, OR = 19.2 (4.4-82.7); MPE vs. Tolerant: P = 0.004, OR = 6.2 (1.6-23.3)

In still another embodiment in the present invention, different SNPs can be combined for assessing the risk of phenytoin-induced adverse drug reactions. It is found that a combination of rs1057910 (CYP2C9*3), rs3758581, rs17110192, rs9332245 or rs1592037 belonging to a haplotype can increase the statistical significance of association with phenytoin-induced SJS/TEN/DRESS comparing to phenytoin tolerant controls. Especially when patients carry both rs1057910 and rs3758581 or rs17110192 have more significant association with phenytoin-induced SJS/TEN/DRESS (see Table 3).

TABLE 3

Statistical analysis of major SNPs associated with phenytoin-induced SJS/TEN/DRESS

| | | PHT-Case (n = 126) | | Control (n = 95) | | Fisher's test | Chi-square | Odds ratio | 95% CI |
|---|---|---|---|---|---|---|---|---|---|
| 6 SNPs | rs1592037, rs9332245, rs1057910, rs3758581, rs4986893, rs17110192 | 2 | 124 | 0 | 95 | 0.50761004 | 0.21731708 | 3.0645 | 0.137-68.746 |
| 5 SNPs | rs1592037, rs9332245, rs1057910, rs3758581, rs17110192 | 29 | 97 | 0 | 95 | 1.93E-08 | 5.30E-07 | 56.8041 | 3.4201-943.446 |
| 4 SNPs | rs1592037, rs1057910, rs3758581, rs17110192 | 29 | 97 | 0 | 95 | 1.93E-08 | 5.30E-07 | 56.8041 | 3.420-943.446 |
| | rs1592037, rs9332245, rs1057910, rs17110192 | 31 | 95 | 1 | 94 | 9.93E-08 | 8.40E-07 | 30.6737 | 4.103-229.311 |
| | rs1592037, rs9332245, rs3758581, rs17110192 | 29 | 97 | 2 | 93 | 2.7454E-06 | 0.00000936 | 13.9021 | 3.226-59.915 |
| 3 SNPs | rs1057910, rs3758581, (rs17110192/rs9332245) | 30 | 96 | 0 | 95 | 9.50E-09 | 3.10E-07 | 59.375 | 3.578-985.443 |
| | rs9332245, rs17110192, (rs3758581/rs1592037) | 29 | 97 | 3 | 92 | 1.3629E-05 | 0.0000328 | 9.1684 | 2.700-31.131 |
| | rs1592037, rs9332245, rs3758581 | 29 | 97 | 2 | 93 | 2.7454E-06 | 0.00000936 | 13.9021 | 3.226-59.915 |
| | rs1592037/rs9332245/ rs3758581/rs17110192 | 30 | 96 | 3 | 92 | 7.3945E-06 | 0.00002005 | 9.5833 | 2.827-32.487 |
| 2 SNPs | rs1057910, rs17110192 | 31 | 95 | 1 | 94 | 9.93E-08 | 8.40E-07 | 30.6737 | 4.103-229.311 |
| | rs1057910, rs3758581 | 30 | 96 | 0 | 95 | 9.50E-09 | 3.10E-07 | 59.375 | 3.5778-985.443 |
| | rs1057910, (rs1592037/ rs9332245/rs3758581) | 30 | 96 | 1 | 94 | 2.05E-07 | 1.42E-06 | 29.375 | 3.926-219.805 |

Example 2

HLA Alleles and Phenytoin-Related SCAR

The HLA susceptibility of phenytoin-related cutaneous adverse reactions was analyzed due to the presence of immunological characteristics in the disease. Specific oligonucleotide primers and probes were used to identify the HLA-A, HLA-B and HLA-DRB1 genotype of phenytoin-ADRs patients and tolerant controls. The results indicated that HLA-A*0207, HLA-A*2402, HLA-B*1301, HLA-B*1502, HLA-B*4001, HLA-B*4609, HLA-B*5101, HLA-DRB1*1001 or HLA-DRB1*1502 were significantly associated with phenytoin-induced ADRs (SJS/TEN, DRESS, or MPE) (see Table 4 to 6). The data shows that HLA-B*1301 allele significantly increased frequencies among patients with phenytoin-ADRs compared to the tolerant controls. There were 15 SJS/TEN patients (28.3%) and 12 DRESS patients (46.2%) carried HLA-B*1301, while only 14 tolerant patients (11.9%) carried this genotype (SJS/TEN vs. tolerant controls: P=0.001, OR=3.8 (1.7-8.5); DRESS vs. tolerant controls: P=2×10$^{-4}$, OR=6.4 (2.5-16.5)). However, this association was not significant in MPE (MPE vs. Tolerant controls: P=0.296, OR=1.7 (0.7-3.7)). HLA-B*5101 allele was also associated with phenytoin-induced ADRs. There were 13.2% SJS/TEN patients, 19.2% DRESS patients and 15.6% MPE patients carried HLA-B*5101, while only 5 tolerant controls (4.2%) carried this genotype (SJS/TEN vs. tolerant controls: P=0.05, OR=3.4; DRESS vs. tolerant controls: P=0.018, OR=5.4; MPE vs. tolerant controls: P=0.009, OR=4.2). In a further embodiment, the present invention provides a method and kits of assessing the risk of phenytoin-induced adverse drug reactions comprising the step of identifying the presence of HLA genotypes, including HLA-A, HLA-B and HLA-DRB1.

Our previous study has showed that HLA-B*1502 allele was strongly associated with carbamazepine-induced SJS/TEN (Chung W H et al, 2004). In still a further embodiment of the present invention, HLA-B*1502 allele is used for assessing the risk of phenytoin-induced adverse drug reactions, and the results showed that HLA-B*1502 was associated with phenytoin-induced ADRs. There were 12 SJS/TEN patients (22.6%) carried HLA-B*1502, while only 9 tolerant controls (7.6%) carried this genotype. HLA-B*1502 allele significantly increased frequencies among the phenytoin-induced SJS/TEN patients compared to the tolerant controls (SJS/TEN vs. tolerant: P=0.01, OR=3.5 (1.4-9.0)). However, this association was not seen in phenytoin-induced DRESS and MPE (P>0.05).

In addition, in the present invention, we also found that HLA-B*4609 allele significantly increased frequencies among the phenytoin-induced DRESS patients compared to the tolerant controls (DRESS vs. tolerant controls: P=0.032, OR=19.7 (0.9-449.8)) and HLA-A*0207 allele was also associated with phenytoin-induced DRESS (DRESS vs. tolerant controls: P=0.024, OR=4.6 (1.3-16.2)). Moreover, HLA-DRB1*1001 was found to be associated with phenytoin-induced MPE (MPE vs. tolerant controls: P=0.02, OR=13.2); HLA-DRB1*1502 was found to be associated with phenytoin-induced SJS/TEN (SJS/TEN vs. tolerant controls: P=0.029, OR=14). In contrast, HLA-A*2402 and HLA-B*4001 allele were showed a protective effect in phenytoin-induced ADRs (decreased allele frequencies in phenytoin-induced ADRs, increased in tolerant controls).

TABLE 4

Associations between HLA-A alleles and phenytoin-induced cutaneous ADR

| HLA-A allele | Tolerant (n = 117) | SJS/TEN (n = 53) | p-value | Odds ratio (95% CI) | DRESS (n = 22) | p-value | Odds ratio (95% CI) | MPE (n = 75) | p-value | Odds ratio (95% CI) |
|---|---|---|---|---|---|---|---|---|---|---|
| 0207 | 7 (6.0%) | 7 (13.2%) | 0.135 | 2.4 (0.8-7.2) | 5 (22.7%) | 0.024 | 4.6 (1.3-16.2) | 9 (12.0%) | 0.182 | 2.1 (0.8-6.0) |
| 2402 | 38 (32.5) | 8 (15.1%) | 0.025 | 0.4 (0.2-0.9) | 4 (18.2%) | 0.214 | 0.5 (0.1-1.5) | 20 (26.7%) | 0.424 | 0.8 (0.4-1.4) |

TABLE 5

Associations between HLA-B alleles and phenytoin-induced cutaneous ADR

| HLA-B allele | Tolerant (n = 118) | SJS/TEN (n = 53) | p-value | Odds ratio (95% CI) | DRESS (n = 26) | p-value | Odds ratio (95% CI) | MPE (n = 77) | p-value | Odds ratio (95% CI) |
|---|---|---|---|---|---|---|---|---|---|---|
| 1301 | 14 (11.9%) | 15 (28.3%) | 0.001 | 3.8 (1.7-8.5) | 12 (46.2%) | 2 × 10$^{-4}$ | 6.4 (2.5-16.5) | 14 (18.2%) | 0.296 | 1.7 (0.7-3.7) |
| 1502 | 9 (7.6%) | 12 (22.6%) | 0.010 | 3.5 (1.4-9.0) | 0 (0.0%) | 0.213 | 0.2 (0.0-4.2) | 8 (10.4%) | 0.605 | 1.4 (0.5-3.8) |
| 5101 | 5 (4.2%) | 7 (13.2%) | 0.050 | 3.4 (1.0-11.4) | 5 (19.2%) | 0.018 | 5.4 (1.4-20.2) | 12 (15.6%) | 0.009 | 4.2 (1.4-12.4) |
| 4609 | 0 (0%) | 0 (0%) | 1.000 | — | 2 (7.7%) | 0.032 | 19.7 (0.9-449.8) | 0 (0%) | 1.000 | — |
| 4001 | 52 (44.1%) | 20 (37.7%) | 0.504 | 0.8 (0.4-1.5) | 9 (34.6%) | 0.393 | 0.7 (0.3-1.6) | 22 (28.6%) | 0.035 | 0.5 (0.3-1.9) |

TABLE 6

Associations between HLA-DRB1 alleles and phenytoin-induced cutaneous ADRs

| HLA-DRB1 allele | Tolerant (n = 117) | SJS/TEN (n = 53) | p-value | Odds ratio (95% CI) | DRESS (n = 22) | p-value | Odds ratio (95% CI) | MPE (n = 75) | p-value | Odds ratio (95% CI) |
|---|---|---|---|---|---|---|---|---|---|---|
| 1001 | 0 (0.0%) | 0 (0.0%) | 1.000 | — | 0 (0.0%) | 1.000 | — | 4 (5.3%) | 0.022 | 13.2 (0.7-253.1) |
| 1502 | 0 (0.0%) | 3 (5.7%) | 0.029 | 14.0 (0.7-285.5) | 0 (0.0%) | 1.000 | — | 0 (0.0%) | 1.000 | — |

Example 3

Combination of CYP2C and HLA Alleles for Predicting Phenytoin-SCAR

We designed kits which consisted reagents and oligo-nucleotide primers and probes for detecting the presence of the risk alleles selected from a panel, comprising rs1057910 (CYP2C9*3), rs3758581, and HLA-B*1502, HLA-B*1301, and HLA-B*5101. The detection of both CYP2C alleles and HLA alleles further improved the sensitivity of test for phenytoin-related SCAR. For example, the sensitivity of a CYP2C genetic test which detects the presence of either rs1057910 or rs3758581, could be improved with the inclusion of HLA-B*15:02 allele in the testing panel, in which the sensitivity will be 55.93%, and the specificity of 90.77%, positive predictive value (PPV) of 77.33%, and negative predictive value (NPV) of 81.94% for predicting phenytoin-SJS/TEN. Furthermore, adding HLA-B*1301 and HLA-B*5101 to CYP2C (rs1057910/rs3758581) genetic screening improved the sensitivity to 67.27% for all types of phenytoin-SCAR, including SJS/TEN and DRESS (eTable S12).

phenytoin and narrow therapeutic window suggesting phenytoin concentrations in plasma may be related to its efficacy and toxicity.

In this study, the phenytoin concentrations during ADR onset were determined from patients' plasma by HPLC analysis and estimated by non-linear pharmacokinetics formula:

$$t = \frac{K_m \times \ln\left(\frac{G_1}{G_2}\right) + (G_1 - G_2)}{V_{max}} \times V_d$$

$K_m = 4$ mg/L (substrate concentration at which the rate of metabolism is one half of $V_{max}$)

$V_{max} = 7$ mg/kg/day (maximum metabolic rate)

$V_d = 0.65$ L/kg (volume of distribution)

$t$: the time (days) between any two phenytoin plasma concentration

Therapeutic levels of phenytoin are usually between 10-20 μg/ml. After taking drug, phenytoin plasma levels of

TABLE 7

Association strength abd characteristics of the combination of CYP2C and HLA alleles for predicting phenytoin-SCAR

| Alleles on CYP2C/HLA genes | | Positive, n | P value | Sensitivity (%) | Specificity (%) | PPV (%) | NPV (%) |
|---|---|---|---|---|---|---|---|
| rs1057910/ rs3758581/ HLA-B*15:02 | 130 Tolerant Control | 12 | | | | | |
| | 110 SCAR | 49 | 3.07 × 10⁻¹⁰ | 44.55 | 90.77 | 80.33 | 65.92 |
| | 59 SJS/TEN | 33 | 1.61 × 10⁻¹¹ | 55.93 | 90.77 | 73.33 | 81.94 |
| | 51 DRESS | 16 | 4.72 × 10⁻⁴ | 31.37 | 90.77 | 57.14 | 77.12 |
| rs1057910/ rs3758581/ HLA-B*1301/ HLA-B*5101 | 130 Tolerant Control | 30 | | | | | |
| | 110 SCAR | 74 | 4.90 × 10⁻¹² | 67.27 | 76.92 | 71.15 | 73.53 |
| | 59 SJS/TEN | 42 | 5.83 × 10⁻¹⁰ | 71.19 | 76.92 | 58.33 | 85.47 |
| | 51 DRESS | 32 | 1.33 × 10⁻⁶ | 62.74 | 76.92 | 51.61 | 84.03 |

Example 4

Variants of CYP2C Genes Delayed Drug Clearance and Resulted in Phenytoin-SCAR

Figure 2:
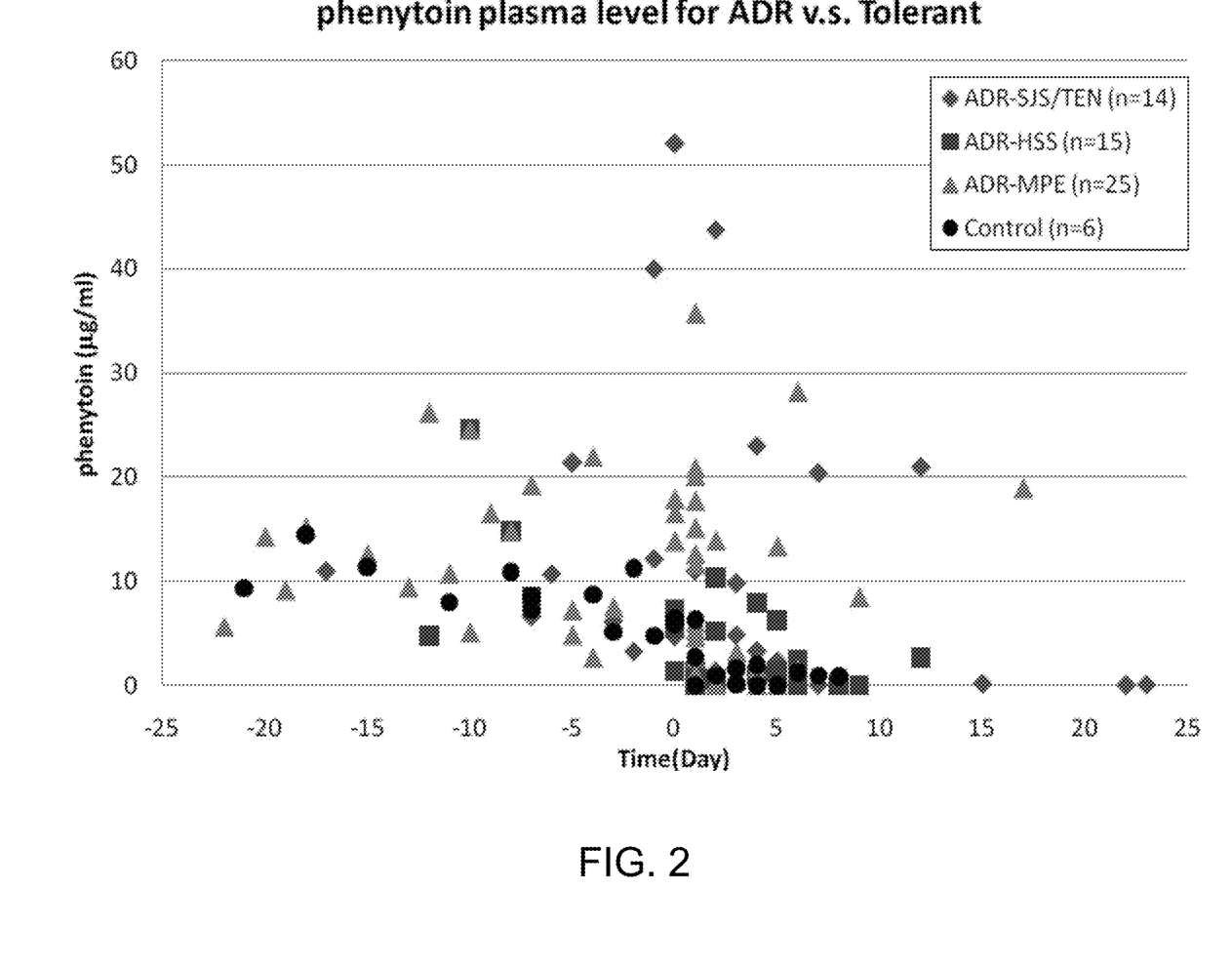
FIG. 2 shows phenytoin plasma level of phenytoin-ADRs and tolerant controls, where the normal therapeutic levels of phenytoin are usually between 10-20 µg/ml and the phenytoin plasma levels of tolerant controls were between 5-15 µg/ml. However, the phenytoin plasma levels of patients with phenytoin-SJS/TEN were 40-50 µg/ml that were higher than that of tolerant controls.

The study also indicates that genetic variants in CYP2C9 as well as in CYP2C19, CYP2C8, CYP2C18 are related to poor metabolic activity for phenytoin and increase its drug accumulation that leads to the risk of phenytoin hypersensitivity. In some embodiments, the method for assessing the risk of phenytoin-induced adverse drug reactions comprises the step of detecting phenytoin concentration in plasma. Since phenytoin is metabolized by liver enzymes, polymorphisms of cytochrome P450 enzymes can affect phenytoin plasma concentrations. The non-linear pharmacokinetics of tolerant control patients were between 5-15 μg/ml. However, in SJS/TEN patients, the phenytoin plasma levels were up to 40-50 μg/ml that were higher than tolerant control patients (SJS/TEN vs. tolerant control: P=0.006; MPE vs. tolerant controls: P=0.004) (see FIG. 2). We also compared the phenytoin plasma levels of patients who carried CYP2Cs variants. The result showed that phenytoin-ADRs patients who carried CYP2C9*3 were with higher phenytoin plasma levels. After analyzing the phenytoin level of 23 phenytoin-ADRs patients, there were 4 patients whose phenytoin levels were lower than 10 μg/ml, 9 patients' phenytoin levels were between 10-20 μg/ml and 10 patients' phenytoin levels were higher than 20 μg/ml. Among these 23 patients, the phenytoin concentrations of 5 patients who carry CYP2C9*3 variant were all higher than 20 μg/ml. The invention proves CYP2Cs variants, especially CYP2C9*3, display poor metabolic activity of phenytoin and can result in hypersensitivity reactions. Defective metabolism of phenytoin may increase the risk of drug accumulation, and leads to its risk to induce severe hypersensitivity reactions, such as SJS/TEN and DRESS.

The CYP2Cs variants and HLA genotypes can be detected by using any method known in the art. Preferably, genomic DNA is hybridized to a probe that is specific for the variant of interest. The probe may be labeled for direct detection, or contacted by a second, detectable molecule that specifically binds to the probe. Alternatively, cDNA, RNA, or protein product of the variant can be detected.

Having described the invention by the description and illustrations above, it should be understood that these are exemplary of the invention and are not to be considered as limiting. Accordingly, the invention is not to be considered as limited by the foregoing description, but includes any equivalents.

REFERENCES

1. Ingelman-Sundberg, M. Pharmacogenomic biomarkers for prediction of severe adverse drug reactions. *N Engl J Med* 358, 637-639 (2008).
2. Bohan, K. H., et al. Anticonvulsant hypersensitivity syndrome: implications for pharmaceutical care. Pharmacotherapy. 27(10), 1425-1439 (2007).
3. Odani, A., et al. Genetic polymorphism of the CYP2C subfamily and its effect on the pharmacokinetics of phenytoin in Japanese patients with epilepsy. *Clin Pharmacol Ther* 62, 287-292 (1997).
4. Shintani, et al. Genetic polymorphisms and functional characterization of the 5'-flanking region of the human CYP2C9 gene: In vitro and in vivo studies. *Clin Pharmacol Ther.* 70(2), 175-182 (2001).
5. Lee, A. Y., Kim, M. J., Chey, W. Y., Choi, J. & Kim, B. G. Genetic polymorphism of cytochrome P450 2C9 in diphenylhydantoin-induced cutaneous adverse drug reactions. *Eur J Clin Pharmacol* 60, 155-159 (2004).
6. Hung, S. I., et al. Common risk allele in aromatic antiepileptic-drug induced Stevens-Johnson syndrome and toxic epidermal necrolysis in Han Chinese. *Pharmacogenomics* 11, 349-356 (2010).
7. Bastuji-Garin S, Rzany B, Stern R S, et al, Shear N H, Naldi L, Roujeau J C. Clinical classification of cases of toxic epidermal necrolysis, Stevens-Johnson syndrome, and erythema multiforme. Arch Dermatol 129, 92-6 (1993).
8. Kardaun S H, Sidoroff A, Valeyrie-Allanore L, Halevy S, Davidovici B B, Mockenhaupt M, et al. Variability in the clinical pattern of cutaneous side-effects of drugs with systemic symptoms: does a DRESS syndrome really exist? Br J Dermatol 156, 609-11 (2007).
9. Chung W H, Chang W C, Lee Y S, Wu Y Y, Yang C H, Ho H C, Chen M J, Lin J Y, Hui R C, Ho J C, Wu W M, Chen T J, Wu T, Wu Y R, Hsih M S, Tu P H, Chang C N, Hsu C N, Wu T L, Choon S E, Hsu C K, Chen D Y, Liu C S, Lin C Y, Kaniwa N, Saito Y, Takahashi Y, Nakamura R, Azukizawa H, Shi Y, Wang T H, Chuang S S, Tsai S F, Chang C J, Chang Y S, Hung S I; Taiwan Severe Cutaneous Adverse Reaction Consortium; Japan Pharmacogenomics Data Science Consortium. Genetic variants associated with phenytoin-related severe cutaneous adverse reactions. JAMA. 2014 Aug. 6; 312(5):525-34

What is claimed is:

1. A method of determining and treating a human patient with epilepsy at a risk for developing an adverse drug reaction in response to phenytoin or fosphenytoin, comprising
    (a) detecting the patient's CYP2C and HLA genotype by
        (i) detecting the presence of a CYP2C9*3 allele by one or more oligonucleotides that specifically hybridizes to the allele; and
        (ii) detecting the presence of a HLA-B*1301 allele by one or more oligonucleotides that specifically hybridizes to the allele in the sample obtained from the patient,
        wherein the presence of the CYP2C9*3 and HLA-B*1301 alleles is indicative of a risk for the adverse drug reaction in response to phenytoin or fosphenytoin; and
    (b) following step an anticonvulsant that is not phenytoin or fosphenytoin to the patient with epilepsy who has the CYP2C9*3 and HLA-B*1301 alleles,
    wherein the adverse drug reaction in response to phenytoin or fosphenytoin is Stevens-Johnson syndrome (SJS), toxic epidermal necrolysis (TEN), or drug reactions with eosinophilia and systemic symptoms (DRESS) and said phenytoin has the following structure:

2. A method of determining and treating a human patient at a risk for developing an adverse drug reaction in response to phenytoin or fosphenytoin, comprising
    (a) detecting the patient's CYP2C and HLA genotype by
        (i) detecting the presence of a CYP2C9*3 allele by one or more oligonucleotides that specifically hybridizes to the allele; and
        (ii) detecting the presence of a HLA-B*1301 allele by one or more oligonucleotides that specifically hybridizes to the allele in the sample obtained from the patient,
        wherein the absence of the CYP2C9*3 and HLA-B*1301 alleles is indicative of the patient having a decreased risk of SJS, TEN or DRESS in response to phenytoin or fosphenytoin; and
    (b) following step (a), administering phenytoin or fosphenytoin to the patient without the CYP2C9*3 and HLA-B*1301 alleles,
    wherein said phenytoin has the following structure:

* * * * *